(12) United States Patent
Kokubo et al.

(10) Patent No.: US 12,029,590 B2
(45) Date of Patent: Jul. 9, 2024

(54) BLOOD PRESSURE SURGE PATTERN DETECTION SYSTEM

(71) Applicant: OMRON HEALTHCARE Co., Ltd., Muko (JP)

(72) Inventors: Ayako Kokubo, Kyoto (JP); Hirotaka Wada, Kyoto (JP); Hiroshi Nakajima, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 275 days.

(21) Appl. No.: 16/561,506

(22) Filed: Sep. 5, 2019

(65) Prior Publication Data

US 2019/0388037 A1     Dec. 26, 2019

Related U.S. Application Data

(63) Continuation of application No. PCT/JP2018/009578, filed on Mar. 12, 2018.

(30) Foreign Application Priority Data

Mar. 15, 2017   (JP) ................................. 2017-050066

(51) Int. Cl.
*A61B 5/021* (2006.01)
*A61B 5/00* (2006.01)

(52) U.S. Cl.
CPC ........ *A61B 5/7264* (2013.01); *A61B 5/02108* (2013.01); *A61B 5/742* (2013.01)

(58) Field of Classification Search
CPC .................. A61B 5/7264; A61B 5/742; A61B 5/02108–02116; A61B 5/7282
See application file for complete search history.

(56) References Cited

U.S. PATENT DOCUMENTS 5,215,096 A * 6/1993 Zapf .................. A61B 5/02225
                                                    600/495
5,680,867 A * 10/1997 Shimazu .............. A61B 5/7264
                                                    600/490

(Continued)

FOREIGN PATENT DOCUMENTS

JP        H09-51880 A      2/1997
JP        2004-261452 A    9/2004

(Continued)

OTHER PUBLICATIONS

Apr. 10, 2018 International Search Report issued in International Patent Application No. PCT/JP2018/009578.

(Continued)

*Primary Examiner* — Meredith Weare
(74) *Attorney, Agent, or Firm* — Oliff PLC

(57) ABSTRACT

The features of blood pressure surges are classified based on blood pressure information, which is one type of biological information. An information processing apparatus includes a classification unit configured to classify a blood pressure surge determined with reference to time-series data of blood pressure values that change in conjunction with heartbeats, into one or more patterns based on a feature point and a feature amount that characterize the blood pressure surge; and a display unit configured to, upon one of the classified patterns being selected, display a waveform that corresponds to the selected pattern, or display a period in the time-series data to which the waveform corresponds.

7 Claims, 14 Drawing Sheets

(56) References Cited

U.S. PATENT DOCUMENTS

| | | | |
|---|---|---|---|
| 9,220,437 B2* | 12/2015 | Dhurandhar | A61B 5/7264 |
| 2005/0190065 A1* | 9/2005 | Ronnholm | G04G 21/025 |
| | | | 340/575 |
| 2007/0156201 A1 | 7/2007 | Rossing | |
| 2008/0200819 A1* | 8/2008 | Lynn | A61B 5/02416 |
| | | | 600/485 |
| 2009/0018453 A1* | 1/2009 | Banet | A61B 5/14551 |
| | | | 600/493 |
| 2010/0017225 A1* | 1/2010 | Oakley | G16H 15/00 |
| | | | 705/2 |
| 2010/0204552 A1 | 8/2010 | Yamamoto et al. | |
| 2013/0296717 A1* | 11/2013 | Takenoshita | A61B 5/7221 |
| | | | 600/479 |
| 2017/0215749 A1* | 8/2017 | Zhuo | A61B 5/02055 |
| 2022/0007951 A1* | 1/2022 | Kokubo | A61B 5/7264 |

FOREIGN PATENT DOCUMENTS

| | | |
|---|---|---|
| JP | 2005-000409 A | 1/2005 |
| JP | 2007-282668 A | 11/2007 |
| JP | 2009-28441 A | 2/2009 |
| JP | 2015-216970 A | 12/2015 |
| JP | 2016-202345 A | 12/2016 |

OTHER PUBLICATIONS

Aug. 20, 2021 Office Action issued in Chinese Patent Application No. 201880017125.1.

\* cited by examiner

BLOOD PRESSURE SURGE PATTERN DETECTION SYSTEM

TECHNICAL FIELD

The present invention relates to an information processing apparatus, a method, and a program that use continuously measured biological information.

BACKGROUND ART

It is known that, when breathing is restarted after apnea, blood pressure rapidly increases and then decreases. Hereinafter, such a rapid blood pressure fluctuation is referred to as a "blood pressure surge" (or simply as a "surge"). Blood pressure information regarding surges occurring in a patient (e.g., the number of occurrences of surges per unit of time) is considered to be helpful for diagnosis or treatment of Sleep Apnea Syndrome (SAS), for example.

For example, Ambulatory Blood Pressure Monitors (ABPMs) are used to acquire patterns of blood pressure fluctuations. An ABPM is a monitor used in such a manner that an arm band is attached to an upper arm of a patient, and a small automatic blood pressure meter is always carried by the patient to regularly measure and record blood pressure (see, for example, JP 2004-261452A).

There is also a technique in which a blood pressure fluctuation pattern can be acquired by integrating blood pressure data intermittently measured across multiple days, without a patient always carrying an apparatus over a prolonged period of time (see, e.g., JP 2007-282668A).

SUMMARY OF INVENTION

However, the blood pressure measurement apparatuses disclosed in JP 2004-261452A and JP 2007-282668A are suitable to detect a blood pressure fluctuation for a day or a week, but it may be difficult to detect a blood pressure surge because continuous measurement is not performed throughout the day.

Also, blood pressure surges may occur a few hundred times a night, and thus, it requires enormous labor to individually check all patterns of blood pressure surges.

The present invention was made with attention given to the aforementioned circumstances, and it is an object thereof to provide an information processing apparatus, a method, and a program that can classify features of blood pressure surges based on blood pressure information, which is one type of biological information.

In order to solve the foregoing problems, the present invention according to a first aspect is directed to an information processing apparatus that includes: a classification unit configured to classify a blood pressure surge determined with reference to time-series data of blood pressure values that change in conjunction with heartbeats, into one or more patterns based on a feature point and a feature amount that characterize the blood pressure surge; and a display unit configured to, upon one of the classified patterns being selected, display a waveform that corresponds to the selected pattern, or display a period in the time-series data to which the waveform corresponds.

According to a second aspect of the present invention, the information processing apparatus further includes a generating unit configured to generate a numerical value that characterizes each of the classified patterns.

According to a third aspect of the present invention, the information processing apparatus further includes a visualization unit configured to visualize and display the time-series data.

According to a fourth aspect of the present invention, the information processing apparatus further includes a standpoint accepting unit configured to accept a standpoint based on which classification of the patterns is made.

According to a fifth aspect of the present invention, the information processing apparatus further includes a target accepting unit configured to accept, out of the classified patterns, a desired target pattern.

According to the first aspect of the present invention, a blood pressure surge determined with reference to time-series data of blood pressure values that change in conjunction with heartbeats is classified into one or more patterns based on a feature point and a feature amount that characterize the blood pressure surge, and when one of the classified patterns is selected, a waveform that corresponds to the selected pattern is displayed, or a period in the time-series data to which the waveform corresponds is displayed. With this, a user can easily recognize at a glance what kinds of blood pressure surges have occurred, and where in the time-series data each kind of blood pressure surge has occurred.

According to the second aspect of the present invention, numerical values that respectively characterize the classified patterns are generated, and thus it is possible to differentiate the features of the classified patterns according to their quantities, and easily recognize a quantitative difference.

According to the third aspect of the present invention, the time-series data is visualized and displayed, and thus it is possible to visually see where in the time-series data periods of blood pressure surges are present. As a result, it is possible to easily recognize time of occurrence of blood pressure surges, and frequency of occurrence of the blood pressure surges.

According to the fourth aspect of the present invention, a standpoint based on which classification of the patterns is made is accepted, and thus a user can set a standpoint based on which classification is made. Thus, a request from a medical doctor or a patient can be responded to since the classification of patterns is possible based on a standpoint desired by the user.

According to the fifth aspect of the present invention, a desired target pattern, out of the classified patterns, is accepted, and thus it is possible to easily check the waveform of blood pressure surges that corresponds to the desired target pattern, and the periods in time-series data of blood pressure values that correspond to the blood pressure surges.

In other words, according to the aspects of the present invention, it is possible to provide an information processing apparatus, a method, and a program that can classify features of blood pressure surges based on blood pressure information, which is one type of biological information.

DESCRIPTION OF EMBODIMENTS

Hereinafter, an information processing apparatus, a method, and a program according to an embodiment of the present invention will be described with reference to the drawings. Note that, in the following embodiment, it is assumed that portions denoted by identical numbers perform the same operations, and redundant description thereof will be omitted.

Figure 1:
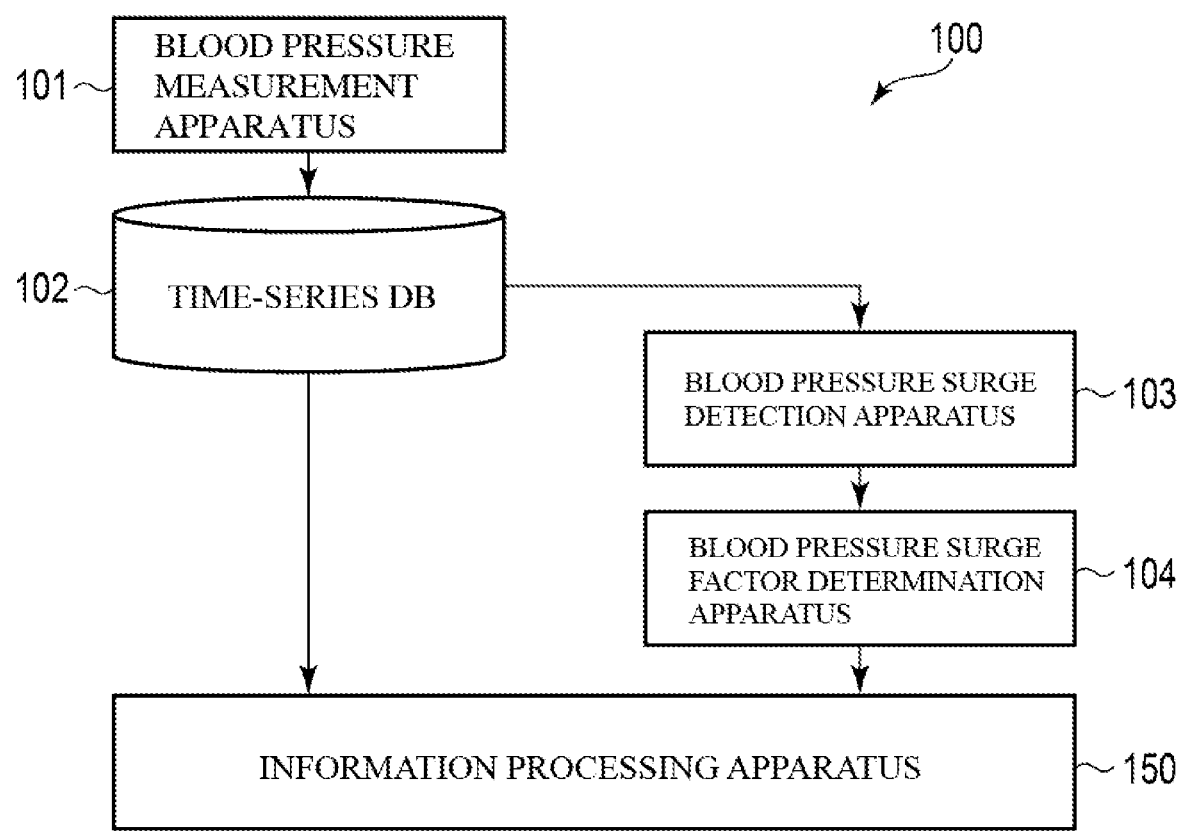
FIG. 1 is a block diagram showing an information processing system according to an embodiment.
Figure 2:
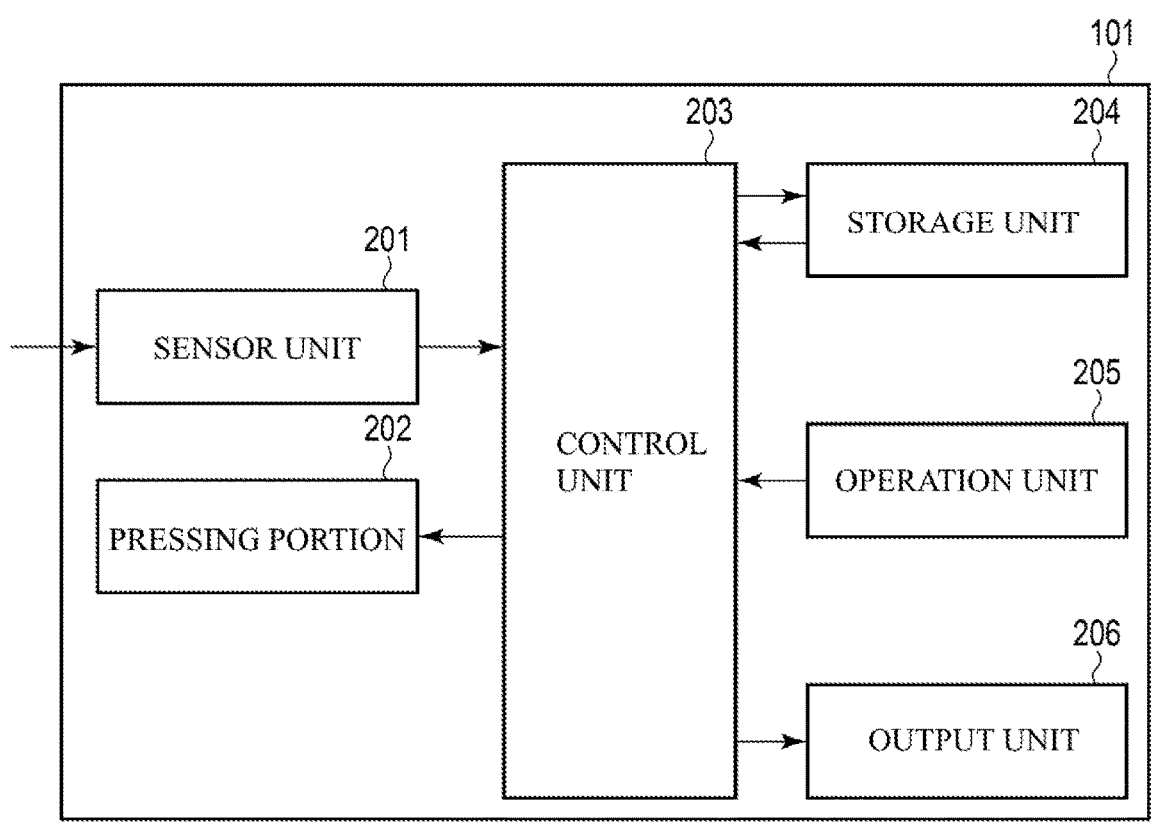
FIG. 2 is a block diagram showing a blood pressure measurement apparatus included in the information processing system of FIG. 1.
Figure 3:
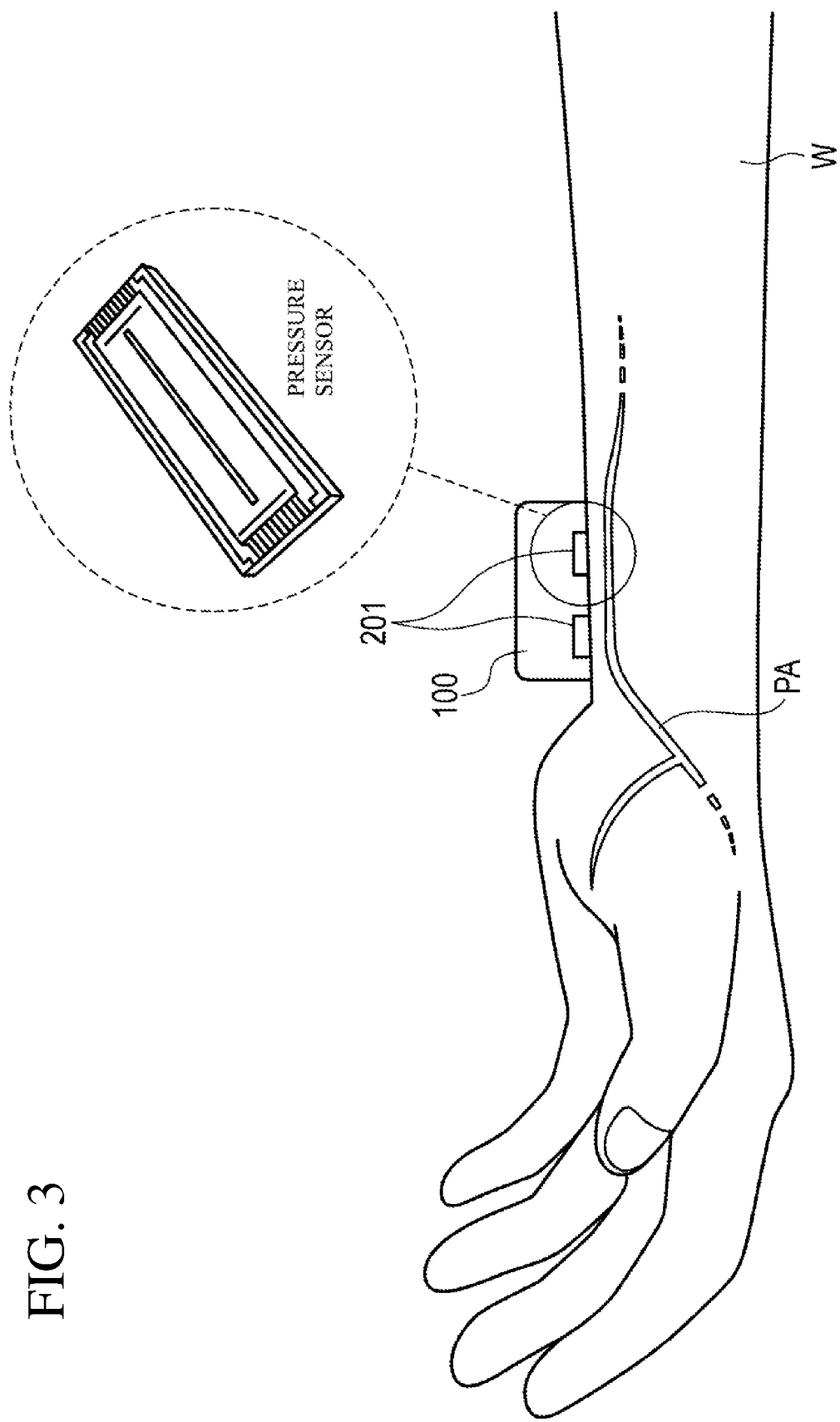
FIG. 3 is a diagram showing an example in which the information processing system of FIG. 1 is attached to the wrist.

An information processing system 100 according to the present embodiment will be described with reference to FIGS. 1 to 5. FIG. 1 is a diagram showing functional blocks of the information processing system 100, and shows a blood pressure measurement apparatus 101 that measures blood pressure that changes in conjunction with heartbeats, a time-series database (abbreviated as "DB") 102, a blood pressure surge detection apparatus 103, a blood pressure surge factor determination apparatus 104, and an information processing apparatus 150. Note that these apparatuses 103, 104, and 105 may be provided in the same apparatus and have different functions, or may be provided in separate apparatuses and have different functions. FIG. 2 is a diagram showing functional blocks of the blood pressure measurement apparatus 101, and shows an example in which blood pressure that changes in conjunction with heartbeats can be measured for each heartbeat, using tonometry. FIG. 3 is a diagram showing an image in which the information processing system 100 is attached, and FIG. 3 is a schematic transparent view from the side of a palm of a hand (viewed in the direction in which the fingers are aligned when the hand is spread out). FIG. 3 shows an example in which pressure pulse wave sensors are aligned in two rows intersecting the radial artery. In FIG. 3, it appears as if the information processing system 100 has merely been placed on the palm side of the arm, but in actuality, the information processing system 100 has been wrapped around the arm.

Figure 4:
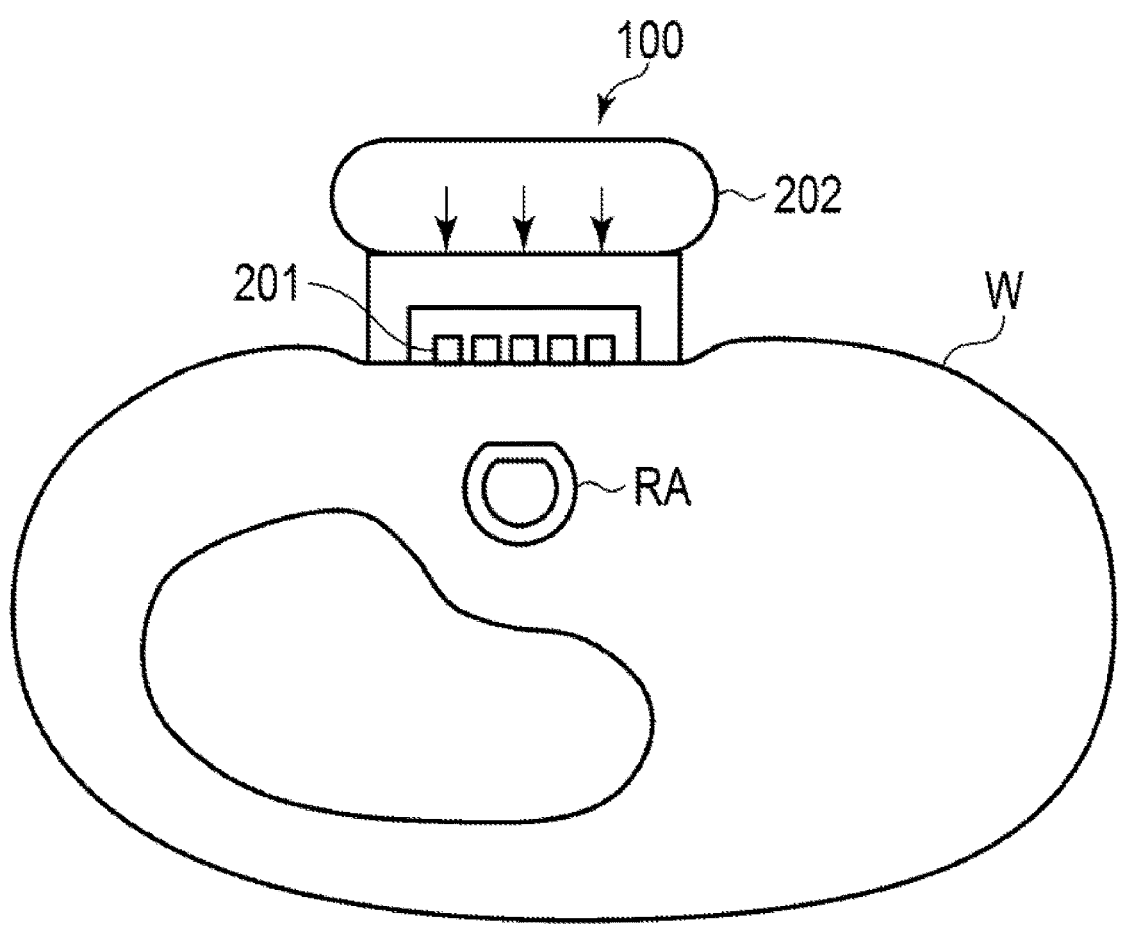
FIG. 4 is a cross-sectional view of a wrist to which the information processing system of FIG. 3 is attached.
Figure 5:
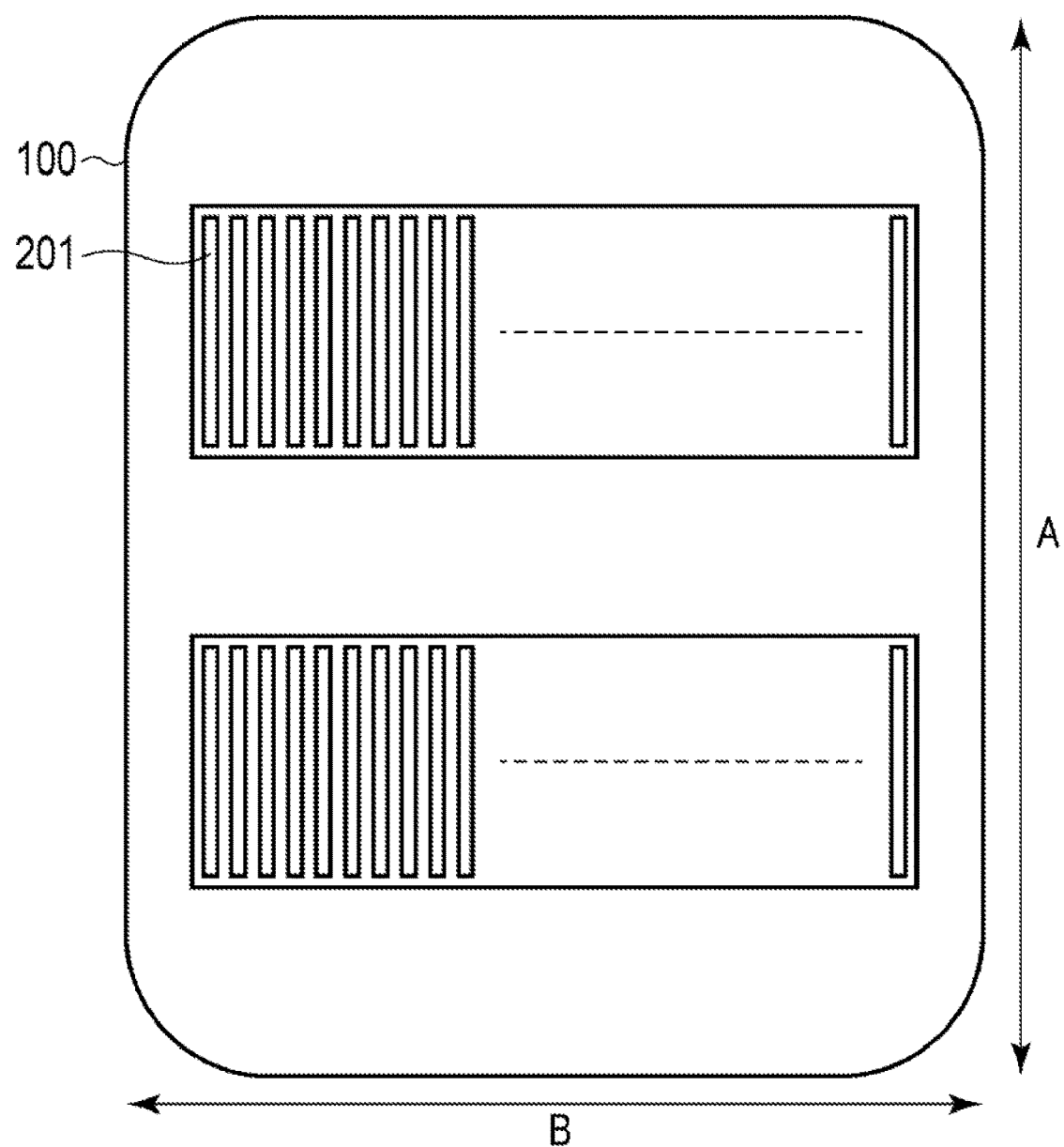
FIG. 5 is a diagram showing an example of an arrangement of sensors of FIGS. 2 to 4.

FIG. 4 is a cross-sectional view of the information processing system 100 and a wrist W at the position of sensor units 201, in a state in which the information processing system 100 is attached to the wrist. FIG. 4 also shows that the radial artery RA is being pressed by the information processing system 100 and the upper portion of the radial artery RA has been flattened. FIG. 5 is a view from the side of the information processing system 100 that comes into contact with a living body, and sensor units 201 are arranged in parallel in two rows on the surface that comes into contact. In the sensor units 201, multiple sensors are aligned in a direction B, which intersects a direction A in which the radial artery extends when the information processing system 100 is attached to the wrist W.

As shown in FIG. 1, the information processing system 100 includes the blood pressure measurement apparatus 101, the time series DB 102, the blood pressure surge detection apparatus 103, the blood pressure surge factor determination apparatus 104, and the information processing apparatus 150.

For example, the information processing system 100 is ring-shaped, wraps like a bracelet around a wrist or the like, and measures blood pressure based on biological information. As shown in FIGS. 2 and 3, the information processing system 100 is arranged such that the sensor units 201 (specifically, the pressure pulse wave sensor) are located above the radial artery. Also, the information processing system 100 is preferably arranged at the same height as the heart.

For example, the blood pressure measurement apparatus 101 measures, using tonometry, the pressure of the pressure pulse wave for each heartbeat, the pressure pulse wave changing in conjunction with heartbeats. Tonometry is a method of measuring pressure pulse waves and determining blood pressure by pressing a blood vessel with a pressure sensor (for example, a pressure pulse wave sensor). If a blood vessel is regarded as a circular tube with a uniform thickness, a relational expression between the inner pressure of the blood vessel (blood pressure) and the outer pressure of the blood vessel (pressure of the pressure pulse wave) can be derived in accordance with Laplace's law with consideration given to the blood vessel walls, regardless of the flow of blood in the blood vessel and whether or not there is a pulse. With this relational expression, under the condition that the blood vessel has been pressed in a pressing plane, the blood pressure can be approximated as being equal to the pressure of the pressure pulse wave by approximating the radii of the outer wall and the inner wall of the blood vessel. Accordingly, thereafter, the pressure of the pressure pulse wave is regarded as having the same value as the value of the blood pressure. As a result, the blood pressure measurement apparatus 101 measures the blood pressure value of the living body to which it is attached for each heartbeat.

Figure 8:
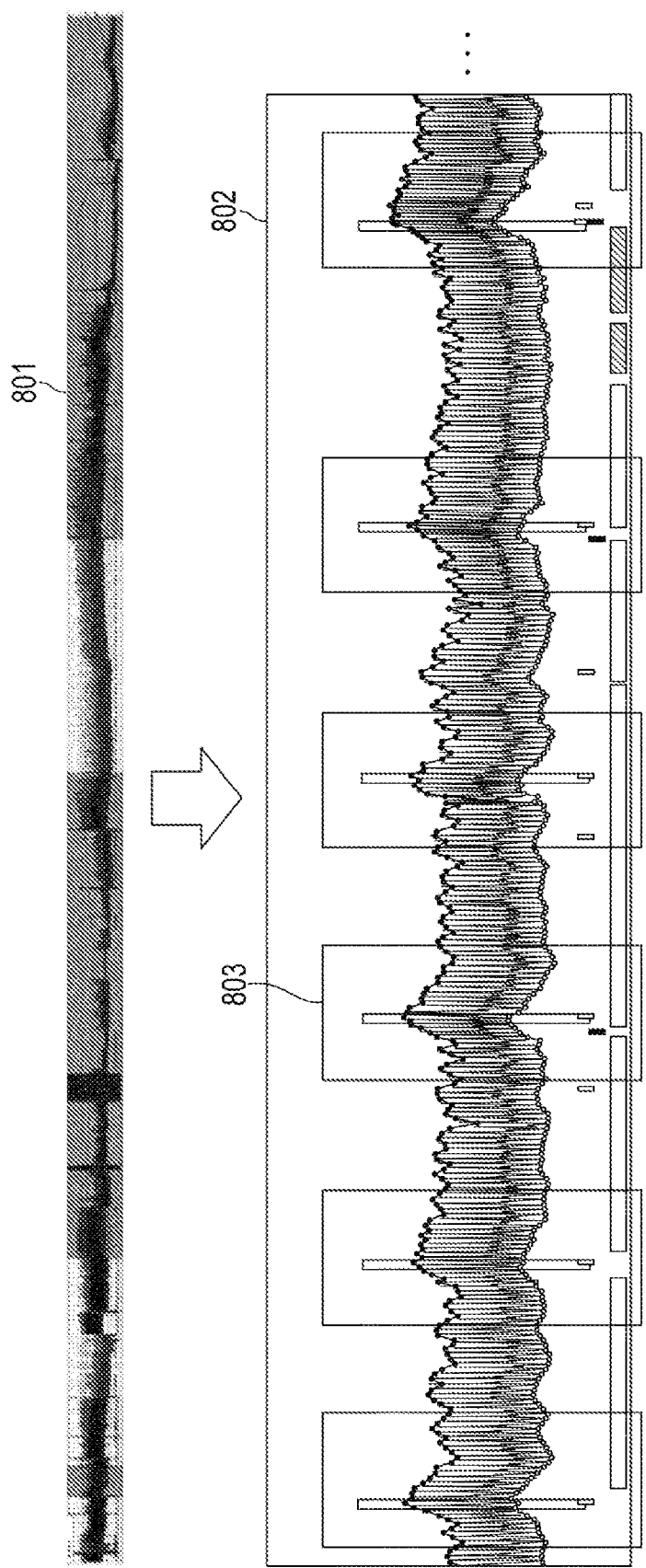
FIG. 8 is a diagram showing time-series data of blood pressure values for one night, and continuous time-series data in which the occurrence of blood pressure surges is recognized.

The time series DB 102 stores time-series data of the blood pressure values measured by the blood pressure measurement apparatus 101. In other words, the blood pressure value measured for each heartbeat by the blood pressure measurement apparatus 101 is recorded along with the time of each measurement. As shown in FIG. 8, the time series DB 102 stores, for example, time-series data 801 of blood pressure values measured at about thirty thousand heartbeats for one night. Time-series data of blood pressure values may include a few hundred blood pressure surges for one night. In a period 802 obtained by enlarging a period in the time-series data 801, several blood pressure surges 803 are seen as shown in a lower portion of FIG. 8.

The blood pressure surge detection apparatus 103 detects blood pressure surges from the time-series data of the blood pressure values. The blood pressure surge detection apparatus 103 detects blood pressure surges based on a feature point and a feature amount of each waveform. Details thereof will be described later with reference to FIG. 10.

Figure 6:
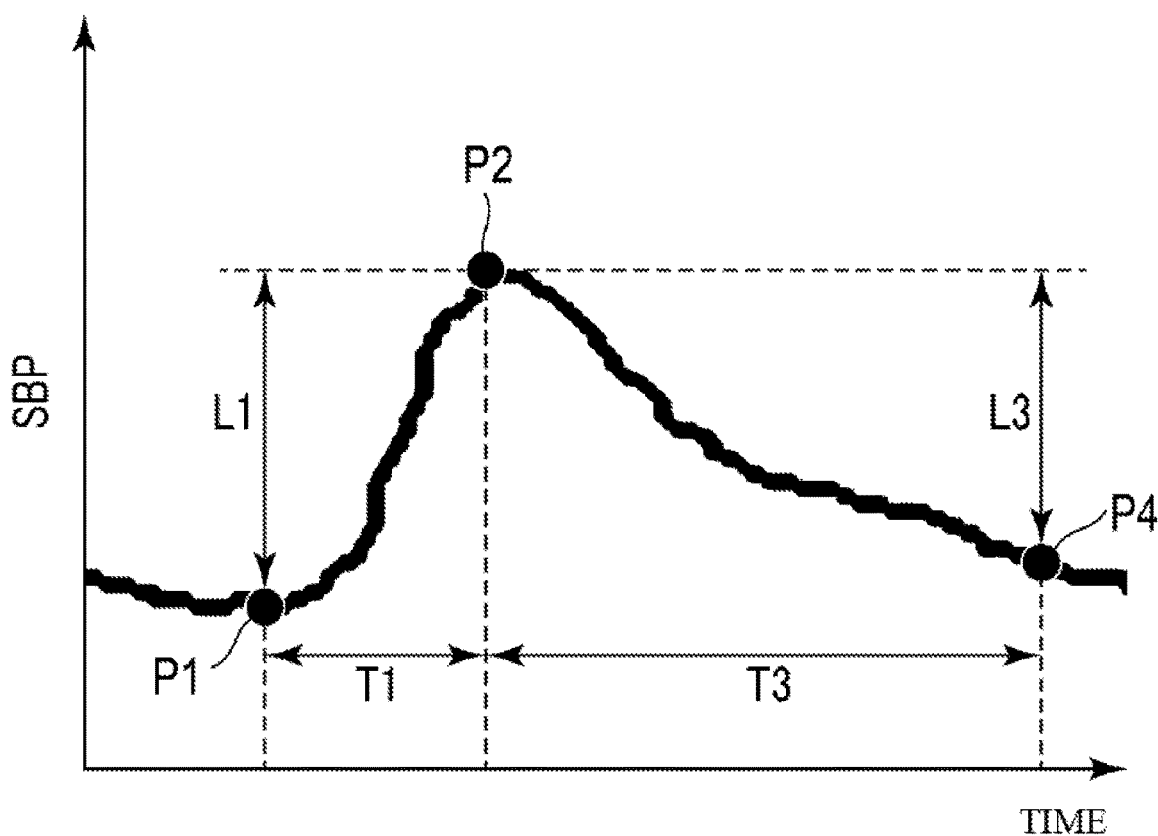
FIG. 6 is a diagram showing an example of feature amounts of a blood pressure surge.

In the blood pressure surge detection apparatus 103, feature amounts of a blood pressure surge corresponds to amounts that relate to blood pressure values and time at points P1, P2, and P4 shown in FIG. 6. The amounts shown in FIG. 6 include, for example, L1, L3, T1, and T3. L1 is a difference between the blood pressure value at the peak point P2 of the blood pressure surge, and the blood pressure value at the start point P1 of the blood pressure surge. L3 is a difference between the blood pressure value at the peak point P2 of the blood pressure surge, and the blood pressure value at the end point P4 of the blood pressure surge. T1 is a difference between the time at the peak point P2 of the blood pressure surge, and the time at the start point P1 of the blood pressure surge, and is referred to as "elevation time". T3 is a difference between the time at the peak point P2 of the blood pressure surge, and the time at the end point P4 of the blood pressure surge, and is referred to as "lowering time".

Here, a waveform that satisfies typical conditions for a blood pressure surge is specified as a blood pressure surge. In other words, conditions for a blood pressure surge are not exactly defined here. However, the information processing system 100 according to the present embodiment is applicable to any condition for a blood pressure surge, by merely replacing the condition for a blood pressure surge described herein with another condition.

Examples of conditions for part of time-series data of blood pressure values showing a typical blood pressure surge may be as follows. The following conditions are expressed by change in the value of systolic blood pressure (SBP). Note that, in the following processing, time-series data of blood pressure values may be subjected to smoothing processing so as to be easily handled, and may be processed into a continuous, smooth, and differentiable curve, for example. It is assume here that a curve that indicates time-series data of blood pressure values has been subjected to smoothing processing so as to be smooth and differentiable. Hereinafter, description will be given with reference to FIG. 6.

After completion of the above-described smoothing processing, as shown in FIG. 6, the peak point P2 that has the maximal value of the time-series data of SBP is selected. Typically, a plurality of peak points P2 are found. Then, the minimum point P1 that is temporally before the peak point P2 and has the minimum value is searched for, and if the minimum point P1 is found, the procedure moves to the next condition, for example. It is determined whether or not the difference L1 in the blood pressure value between P2 and P1 is larger than a threshold (e.g., 20 mmHg). If the difference L1 is smaller than the threshold, it is determined that there is no blood pressure surge. Then, it is determined whether or not the difference T1 in time between the peak point P2 and the minimum point P1 is larger than a certain time period (e.g., 5 heartbeats), and if the difference T1 is larger than the certain time period, it is determined that P1 is the start point of a blood pressure surge. Then, the point P4 that is later than the peak point P2 and at which the differential value is larger than a certain value (e.g., −0.2 mmHg/second) is searched for. Then, it is determined whether or not the difference T3 in time between the point P2 and the point P4 is larger than a certain time period (e.g., 7 heartbeats), and if the difference T3 is larger than the certain time period, it is determined that the point P4 is the end point of the blood pressure surge. Here, if the difference T3 is larger than the certain time period, it is determined that these points P2, P1, and P4 form a blood pressure surge. In this case, the blood pressure surge detection apparatus 103 regards the time period from the point P1 to the point P4 as a blood pressure surge.

The blood pressure surge factor determination apparatus 104 analyzes the feature amounts of blood pressure surges detected by the blood pressure surge detection apparatus 103, and determines respective factors of the blood pressure surges. Examples of a factor of a blood pressure surge include Sleep Apnea Syndrome (SAS), a Rapid Eye Movement (REM) sleep condition, and an arousal response.

The information processing apparatus 150 stores the results of detection of blood pressure surges that were detected and determined by the blood pressure surge detection apparatus 103 and the blood pressure surge factor determination apparatus 104, and provides a user with information regarding blood pressure surges based on the results of detection, in response to an input such as a user's demand. Examples of information regarding blood pressure surges include a summary of the amount of statistics such as classification of the blood pressure surges, the number of events of classified blood pressure surges, representative events, and feature amounts. Furthermore, the information processing apparatus 150 displays, based on these pieces of information, features of the blood pressure surges for the respective selected patterns, and displays where in the enormous quantity of data a certain pattern is located, for example. Details thereof will be described later with reference to FIG. 9.

Then, the blood pressure measurement apparatus 101 will be described with reference to FIG. 2.

The blood pressure measurement apparatus 101 includes: a sensor unit 201; a pressing portion 202; a control unit 203; a storage unit 204; an operation unit 205; and an output unit 206. The sensor unit 201 detects a pressure pulse wave that changes in conjunction with heartbeats. For example, the sensor unit 201 detects the pressure pulse wave for each heartbeat. The sensor unit 201 includes sensors that detect pressure, are arranged on the side of the wrist corresponding to the palm of the hand as shown in FIG. 3, and are normally arranged in one or more rows in the extension direction of the arm as shown in FIG. 3, namely, the sensors being arranged in parallel in two rows.

In each row of the sensor array including the multiple sensors, multiple (e.g., 46) sensors are arranged intersecting (approximately perpendicular to) the extension direction of the arm. The pressing portion 202 is constituted by a pump, a valve, a pressure sensor, and an air bag, and can increase the sensitivity of the sensors by pressing the sensors of the sensor units 201 to the wrist with a suitable pressure due to an air bag inflating. Air is inserted into the air bag through the pump and the valve, the pressure sensor detects the pressure inside of the air bag, and the control unit 203 performs monitoring and controlling to perform adjustment to a suitable pressure. The control unit 203 performs overall control of the blood pressure measurement apparatus 101, receives time-series data of the pulse wave from the sensor units 201, converts the data into time-series data of the blood pressure values, and stored the result in the storage unit 204.

The storage unit 204 stores the time-series data of the blood pressure values, and transmits desired data in response to a request from the control unit 203. The operation unit 205 receives an input from a user or the like from a keyboard, a mouse, a microphone, or the like, and receives an instruction from an external server or the like through a wire or wirelessly. The output unit 206 receives the time-series data of the blood pressure values stored in the storage unit 204 via the control unit 203, and transmits the received time-series data to the outside of the blood pressure measurement apparatus 101.

As shown in FIGS. 3 and 4, the information processing system 100 is arranged on the side of the wrist corresponding to the palm of the hand, and the sensor units 201 of the blood pressure measurement apparatus 101 are arranged so as to be located above the radial artery RA. As indicated by arrows in FIG. 4, the pressing portion 202 presses the sensor units 201 to the wrist W and presses flat the radial artery RA. Note that the information processing system 100 is ring-shaped, wraps like a bracelet around the wrist or the like, and measures the blood pressure, although this is not shown in FIGS. 3 and 4.

Next, the sensor units 201 of the information processing system 100 will be described with reference to FIG. 5. FIG. 5 shows a surface on the side of the sensor units 201 that comes into contact with the wrist W. As shown in FIG. 5, the sensor units 201 include one or more (in this example, two) sensor arrays, and each sensor array includes multiple sensors aligned in the direction B. The direction B is a direction that intersects the direction A in which the radial artery extends in a state in which the information processing system 100 is attached to the measurement subject. For example, the direction A and the direction B may also be perpendicular. For example, 46 sensors (referred to as 46 channels) are arranged in one row. Note that here, the sensors are provided with channel numbers. Also, the arrangement of the sensors is not limited to the example shown in FIG. 5.

Figure 7:
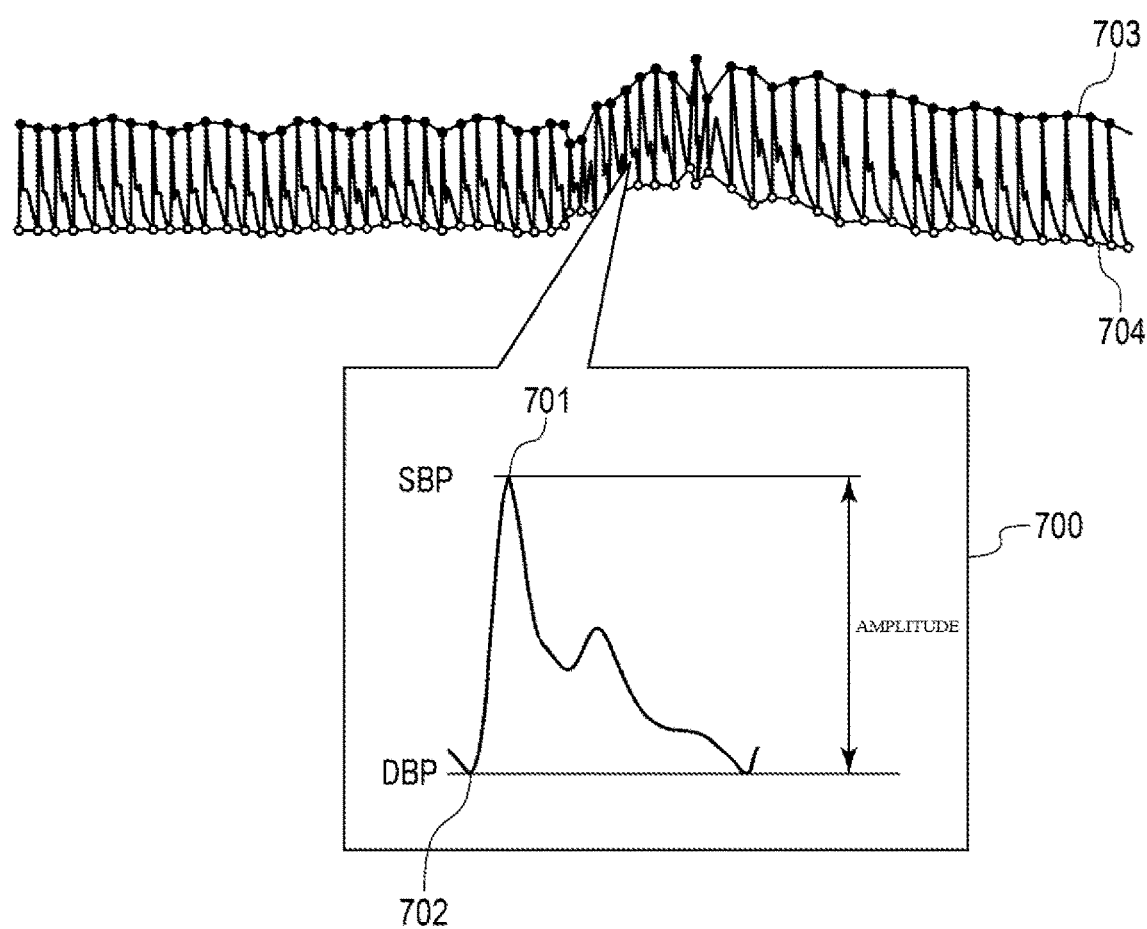
FIG. 7 is a diagram showing changes over time in pressure of pressure pulse waves per heartbeat, and one of the pulse waves.

The sensors generate pressure data by measuring the pressure. Piezoelectric elements that convert pressure into electrical signals can be used as the sensors. A pressure waveform as shown in FIG. 7 is obtained as the pressure data. The result of measuring the pressure pulse wave is generated based on the pressure data output from one sensor (active channel) selected adaptively from among the sensors. The maximum value in the waveform of a pressure pulse wave of one heartbeat corresponds to the SBP, and the minimum value in the waveform of a pressure pulse wave of one heartbeat corresponds to the diastolic blood pressure (DBP).

The blood pressure data can include the result of measuring the pressure pulse wave and the pressure data output from each of the sensors. Also, the information processing system 100 may calculate the time-series data of the blood pressure values based on the result of measuring the pressure pulse wave, and may output the time-series data of the blood pressure values, instead of the result of measuring the pulse wave.

Next, time-series data of blood pressure calculated based on the pressure pulse wave measured by the blood pressure measurement apparatus 101 will be described with reference to FIG. 7. FIG. 7 shows the time-series data of blood pressure calculated based on the pressure of the pressure pulse wave when the pressure of the pressure pulse wave for each heartbeat is measured. Also, FIG. 7 shows a waveform 700 of blood pressure obtained based on one of the pressure pulse waves. The blood pressure obtained based on the pressure pulse wave is detected for each heartbeat as a waveform such as that shown in FIG. 7, and the blood pressure obtained based on the pressure pulse waves is continuously detected. The waveform 700 shown in FIG. 7 is a blood pressure waveform obtained based on the pressure pulse wave of one heartbeat, and a pressure value indicated by reference number 701 corresponds to the SBP, and a pressure value indicated by reference number 702 corresponds to the DBP. As indicated by the time series of the blood pressure corresponding to the pressure pulse wave of FIG. 7, typically, the SBP 703 and the DBP 704 of the blood pressure waveform fluctuate for each heartbeat.

Note that, in the embodiment, the sensor units 201 detect, for example, the pulse wave of the radial artery that extends in a measurement target region (e.g., the left wrist) as a change in pressure (tonometry method). However, the present invention is not limited to this. The sensor units 201 may each include a light emitting element that emits light toward an artery that extends in a corresponding portion of the measurement target region, and a light receiving element that receives the reflected light (or transmitted light) of this light, and the sensor units 201 may detect the pulse wave of the artery as a change in volume (photoelectric method). Also, the sensor units 201 may each include a piezoelectric sensor that comes into contact with the measurement target region, and may detect a deformation due to the pressure of an artery that extends in a corresponding portion of the measurement target region as a change in electric resistance (piezoelectric method). Also, the sensor units 201 may each include a transmission element that transmits a radio wave (transmission wave) toward an artery that extends in a corresponding portion of the measurement target region, and a reception element that receives the reflected wave of this radio wave, and may detect a change in the distance between the artery and the sensor due to the pulse wave of the artery, as a phase shift between the transmission wave and the reflected wave (radio wave irradiation method). Note that, if a physical amount that can be used to calculate blood pressure can be observed, a method other than the above-described methods may also be applied.

Figure 9:
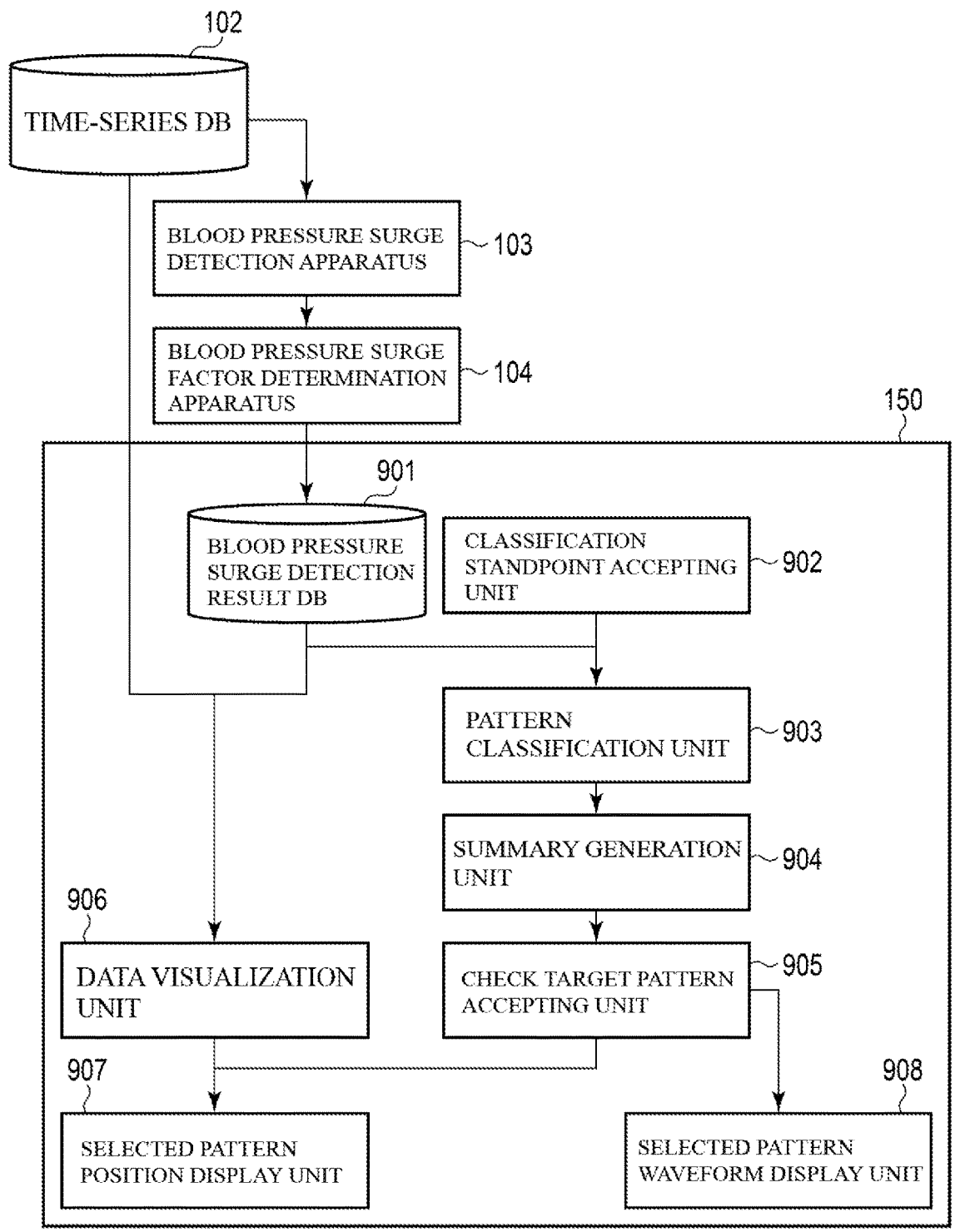
FIG. 9 is a block diagram showing in detail the information processing apparatus included in the information processing system according to the embodiment.

Next, the information processing apparatus 150 will be described with reference to FIG. 9. FIG. 9 shows the information processing apparatus 150 in detail.

The information processing apparatus 150 includes: a blood pressure surge detection result DB 901; a classification standpoint accepting unit 902; a pattern classification unit 903; a summary generation unit 904; a check target pattern accepting unit 905; a data visualization unit 906; a selected pattern position display unit 907; and a selected pattern waveform display unit 908.

The blood pressure surge detection result DB 901 stores results obtained by the blood pressure surge detection apparatus 103 and the blood pressure surge factor determination apparatus 104. In other words, the blood pressure surge detection result DB 901 stores, for each detected blood pressure surge, feature amounts of the blood pressure surge, and an occurrence factor of the blood pressure surge.

The classification standpoint accepting unit 902 accepts, from a user, an instruction relating to classification of blood pressure surges. The instruction from the user includes, for example, the degree of risk of a blood pressure surge, an occurrence factor of a blood pressure surge, and the shape of the blood pressure waveform of a surge. In this context, "risk" refers to the danger of developing brain cardiovascular events.

The pattern classification unit 903 classifies the detection results of the blood pressure surges stored in the blood pressure surge detection result DB 901 based on the shape of the blood pressure waveform of the surges, in accordance with the instruction from the classification standpoint accepting unit 902. If the classification is made only based on the shape of the blood pressure waveform (pattern) of the surges, pattern classification will be performed with unsupervised clustering. Note that the blood pressure waveform of one surge may also belong to a plurality of patterns.

The summary generation unit 904 generates, for each pattern, a summary of the amount of statistics that belong to the pattern, such as the number of events (for example, the number of surges), the surge, and the feature amounts, for example.

The check target pattern accepting unit 905 accepts, from a user, an instruction regarding a check target pattern, which is desired to be checked by the user, from among the patterns classified by the pattern classification unit 903.

The selected pattern waveform display unit 908 displays the blood pressure waveform of the surges of the pattern selected by the user using the check target pattern accepting unit 905 on a monitor or the like.

The data visualization unit 906 displays time-series data in a desired period, extracted from the time-series data stored in the time series DB 102, in a format that can be checked by the user. The data visualization unit 906 visualizes and displays, for example, time-series data of the blood pressure values for one night from falling asleep to waking up. For example, the data visualization unit 906 expresses time-series data of the blood pressure values in a graph with the horizontal axis representing the time from falling asleep to waking up and the vertical axis representing the blood pressure values, and displays the graph on the monitor or the like.

Note that, if the blood pressure waveform of one surge belongs to a plurality of patterns, when a summary is generated or data is visualized, the blood pressure waveform may be set to belong to the plurality of patterns, or may be separated individually to be set to belong to any of the patterns.

The selected pattern position display unit 907 displays where in the time-series data visualized by the data visualization unit 906 the selected pattern is located at, the selected pattern being set as a check target by the user using the check target pattern accepting unit 905.

Figure 10:
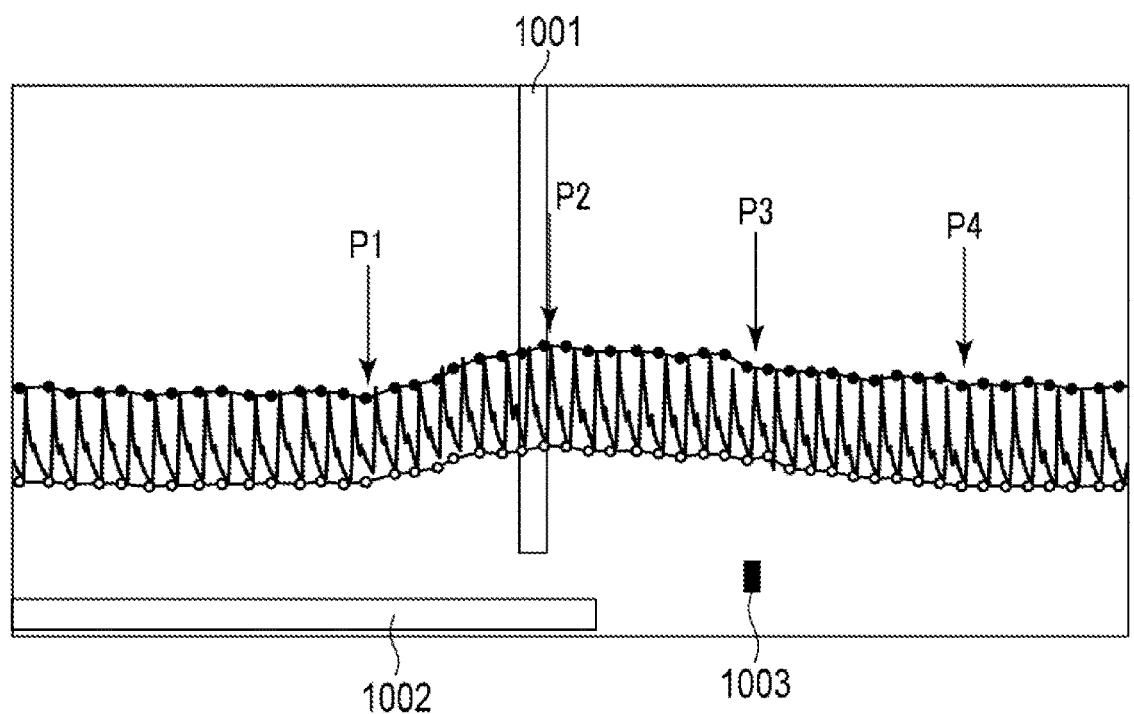
FIG. 10 is a diagram showing another example of feature amounts of a blood pressure surge.

Next, feature amounts of a blood pressure surge stored in the blood pressure surge detection result DB 901 will be described with reference to FIG. 10.

Feature points of a blood pressure surge may correspond to arbitrary points on a continuous curve of time-series data of blood pressure values, but typically include the start point P1 of the blood pressure surge, the peak point P2 of the blood pressure surge, and the end point P4 of the blood pressure surge. In addition, a point P3, which is located between P2 and P4 and is set based on P1 and P2, may also be set as a feature point. Also, feature amounts of a blood pressure surge include: for example, (1) a difference in time between feature points; (2) a fluctuation amount of the blood pressure values between feature points; (3) an area defined by an envelope curve obtained by (smoothly) connecting systolic blood pressure values; (4) an inclination when the blood pressure values increase or decrease, the fluctuation amount thereof, and/or, the fluctuation time period thereof; and (5) a total time in which the blood pressure value exceeds a certain blood pressure reference value. Furthermore, feature amounts of a pressure pulse wave in an area interposed between feature points of a surge may also be used. Feature amounts of a pressure pulse wave include, for example, a ratio of reflected waves to ejection waves, that is to say, an Augmentation Index (AI), a difference in time between the maximal point and the minimum point of the pressure pulse wave, a difference in blood pressure value, and the like.

Next, a state in which time-series data of blood pressure values visualized by the data visualization unit 906, and selected pattern waveforms displayed by the selected pattern waveform display unit 908 are displayed on the monitor will be described with reference to FIG. 11.

The data visualization unit 906 visualizes and displays, on the monitor, time-series data 1103 of the blood pressure values for one night obtained from the time series DB 102, for example. Together with the time-series data 1103, for example, a ratio 1101 and a representative event/number table 1102 of patterns are displayed on the monitor, the ratio 1101 and the representative event/number table 1102 being generated by the summary generation unit 904.

The ratio 1101 is, for example, a ratio of the number of blood pressure surges that correspond to representative events, to the total number of blood pressure surges of the time-series data 1103. The pattern classification unit 903 may also display, in addition to the ratio 1101, an average, a standard deviation, or the like of the fluctuation amounts of the blood pressure surges that are calculated for each of the patterns that correspond to the representative events. The representative event/number table 1102 includes figures of the representative events (or the feature amounts), and the total number of blood pressure surges and the number of patterns that correspond to the representative events.

Next, the relationship between a pattern selected by the selected pattern waveform display unit 908 and the time-series data 1103 will be described with reference to FIG. 12.

Figure 11:
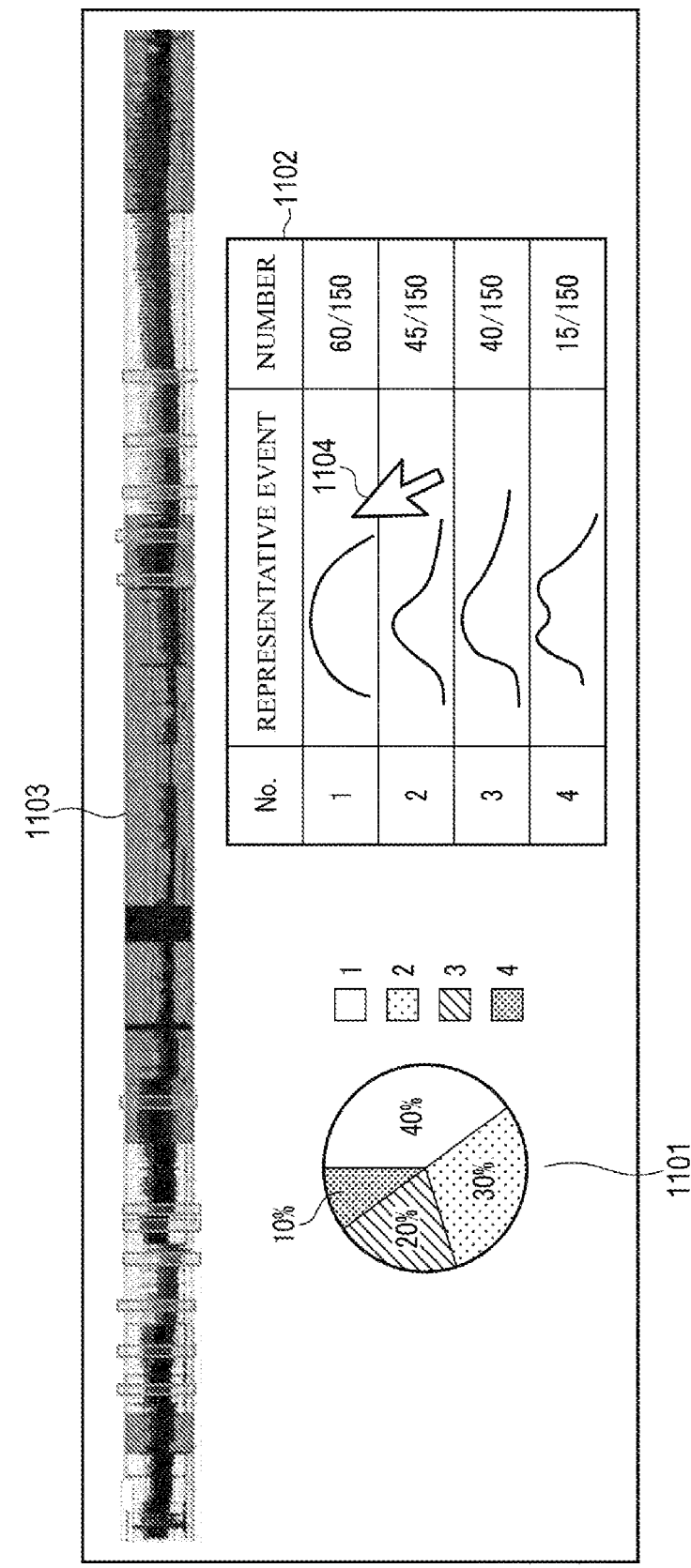
FIG. 11 is a diagram showing an example in which time-series data is visualized by a data visualization unit shown in FIG. 9, a summary of blood pressure surge patterns is generated by a summary generation unit, and display is performed by a display unit.
Figure 12:
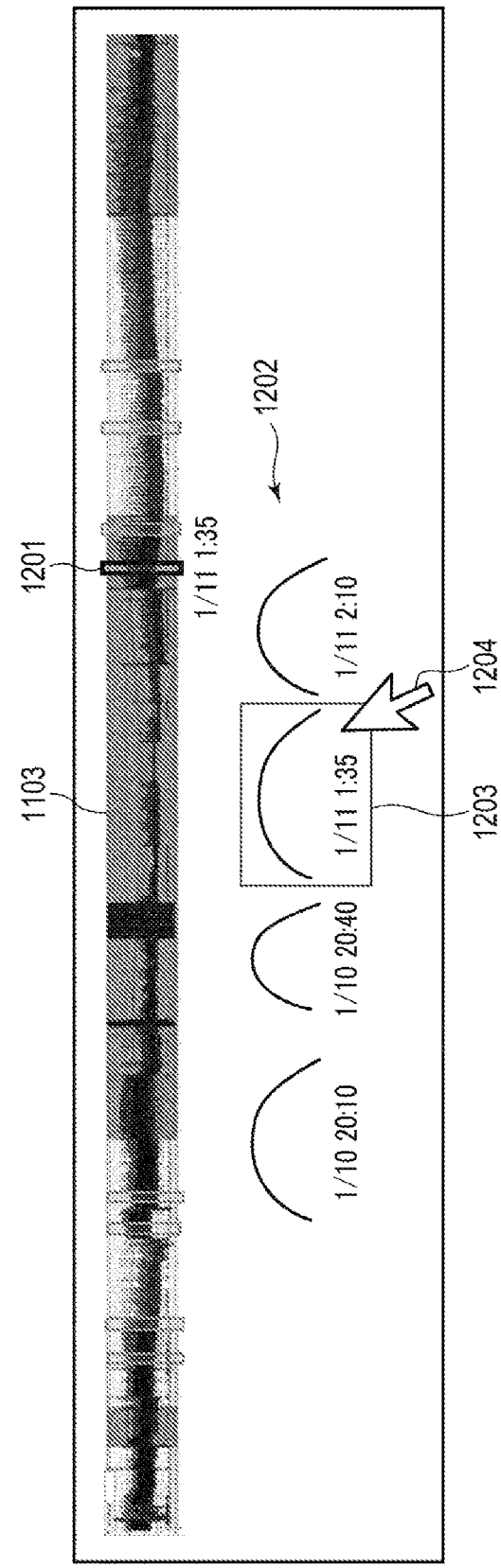
FIG. 12 is a diagram showing an example in which patterns are displayed by a selected pattern waveform display unit shown in FIG. 9, and a selected pattern position display unit is located at a selection pattern position.

If, on the picture plane shown in FIG. 11, a pattern No. 1 is assumed to have been selected by a user (selected using a cursor 1104 or the like), the picture plane is changed to the picture plane of FIG. 12, where a plurality of surges that belong to the pattern No. 1 are displayed (1202). The plurality of surges that correspond to this pattern may also be displayed with information regarding the time at which the corresponding surge has occurred (such as, for example, time and date "1/11 1:35" shown in FIG. 12). In other words, the time at which all of the surges that correspond to the pattern selected by the user have occurred, and the positions thereof are displayed on the time-series data. Furthermore, for example, all of the surges that correspond to all of the patters of the event/number table 1102 shown in FIG. 11 may be displayed on the time-series data 1103 in different colors for the patterns. Upon any of the plurality of displayed surges 1202 being selected by the user (here, a surge 1203 being selected), the selected pattern position display unit 907 displays, on the monitor, a position 1201 of the surge 1203 on the time-series data 1103. For example, if the user brings the cursor to a desired surge (or if the user selects the desired surge), the position of this surge on the time-series data 1103 is displayed. For example, if the user moves the cursor over (mouses over) a desired surge, the position on the temporal axis of the time-series data 1103 at which the desired surge is present is highlighted.

Figure 13:
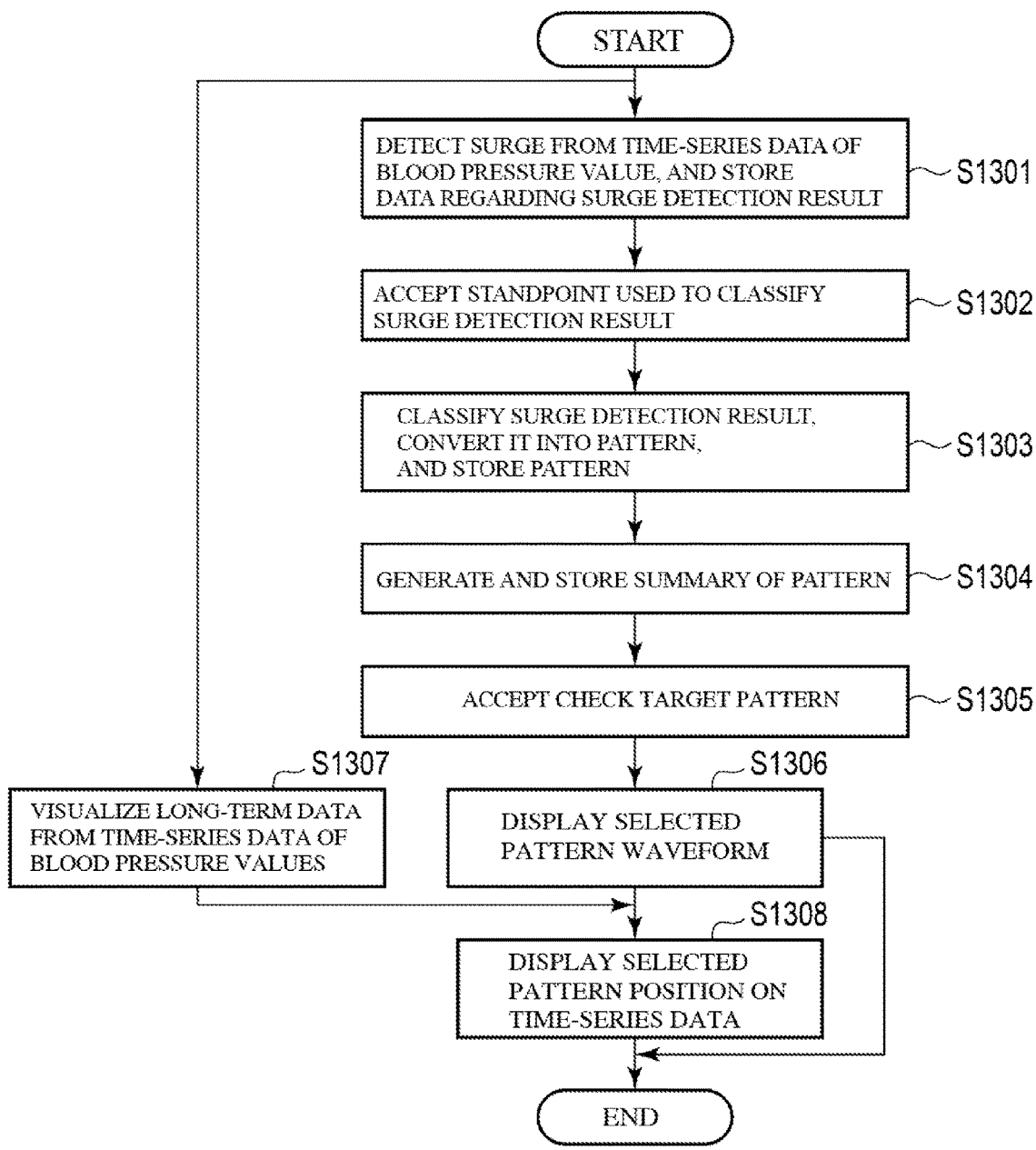
FIG. 13 is a flowchart showing an example of an operation of the information processing system of FIG. 9.

Next, an operation of the information processing apparatus 150 will be described with reference to FIG. 13.

The blood pressure surge detection apparatus 103 detects blood pressure surges from time-series data of blood pressure values stored in the time series DB 102, and stores data regarding the results of detection of the blood pressure surges, together with factors of the blood pressure surges determined by the blood pressure surge factor determination apparatus 104, in the blood pressure surge detection result DB 901 (step S1301).

The classification standpoint accepting unit 902 accepts a standpoint based on which the results of detection of the blood pressure surges are classifies (step S1302). Specifically, for example, a user interface is used to select a standpoint.

The pattern classification unit 903 classifies the results of detection of the blood pressure surges based on the standpoint selected by the classification standpoint accepting unit 902, converts the classified blood pressure surges into patterns, and stores the patterns (step S1303). The summary generation unit 904 generates a summary for each of the converted patterns made by the pattern classification unit 903 (step S1304).

Of a plurality of patterns included in the summary generated in step S1304, the check target pattern accepting unit 905 accepts a pattern (check target pattern) checked by the user (step S1305).

The selected pattern waveform display unit 908 displays all of the waveforms of the representative patterns desired by the user (step S1306).

On the other hand, the data visualization unit 906 visualizes long-term data (e.g., data during sleep for one night) extracted from the time-series data of the blood pressure values stored in the time series DB 102 (step S1307).

The positions of all of the waveforms of the representative patterns that were desired by the user and displayed in step S1306 are displayed on the time-series data 1103 (step S1308). Then, upon the user selecting a specific waveform (by, for example, moving the cursor over (mousing over) this waveform), the position of this waveform on the time-series data 1103 is, for example, highlighted so as to be immediately recognized by the user.

According to the above-described embodiment, it is possible to easily check what kind of blood pressure surge has occurred and when this blood pressure surge has occurred, making it possible for the user (a medical doctor or a patient) to easily recognize a specific type of blood pressure surge in detail. Furthermore, according to the present embodiment, multiple patterns of blood pressure fluctuations can be classified based on various standpoints, a list of the patterns can be viewed, and a user can recognize where in the time series the surges are present that correspond to the pattern details of which the user desires to check. Accordingly, it is easier to recognize the features of a patient. Also, it is possible to easily recognize a rough symptom of the patient.

Figure 14:
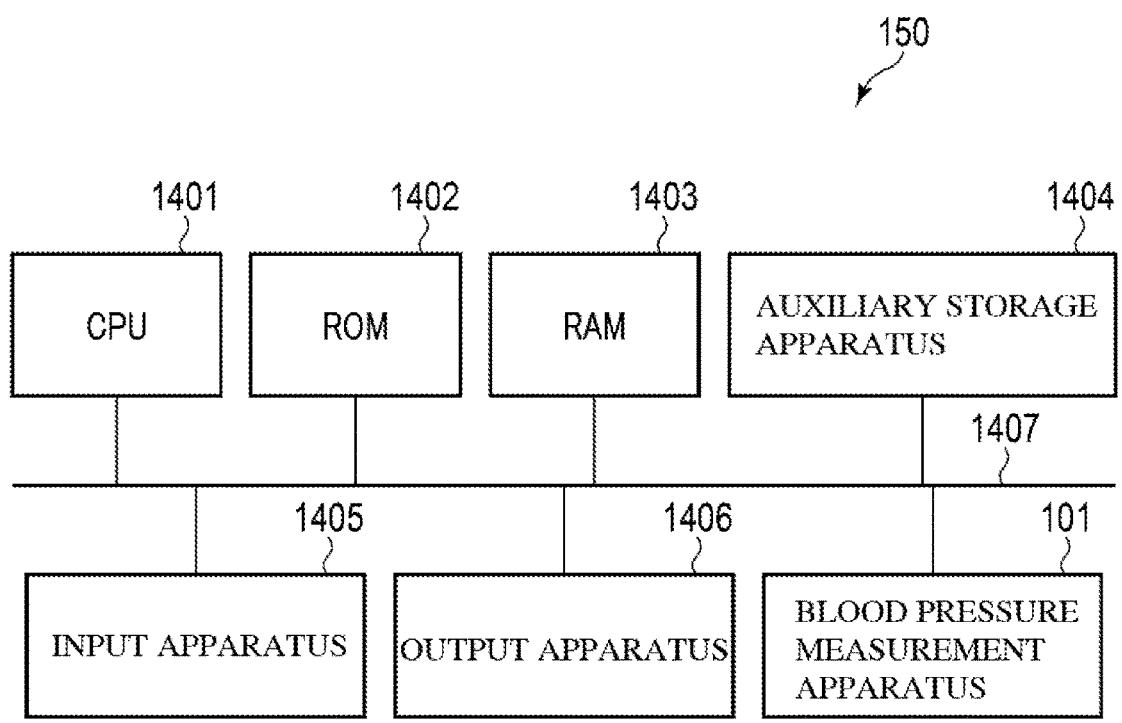
FIG. 14 is a diagram showing an example of implementing the information processing system of FIG. 1 or 15.

Next, an example of a hardware configuration of the information processing system 100 will be described with reference to FIG. 14.

The information processing apparatus 150 and the blood pressure measurement apparatus 101 may be separate apparatuses. The information processing apparatus 150 includes a CPU 1401, a ROM 1402, a RAM 1403, an auxiliary storage apparatus 1404, an input apparatus 1405, an output apparatus 1406, and a blood pressure measurement apparatus 101, and these elements are connected to each other via a bus system 1407. The above-described functions of the information processing apparatus 150 can be realized by the CPU 1401 reading out a program stored in a computer-readable recording medium (ROM 1402) and executing the read-out program. The RAM 1403 is used by the CPU 1401 as a work memory. In addition, the auxiliary storage apparatus 1404 provided with, for example, a hard disk drive (HDD) or a solid-state drive (SDD) may also be included, used as the time series DB 102 and the blood pressure surge detection result DB 901, and further store a program.

For example, the input apparatus 1405 includes a keyboard, a mouse, and a microphone, and receives operations from a user. For example, the input apparatus 1405 includes an operation button for causing the blood pressure measurement apparatus 101 to start measurement, an operation button for performing calibration, and an operation button for starting or stopping communication. For example, the output apparatus 1406 includes a display apparatus such as a liquid crystal display apparatus, and a speaker. The information processing apparatus 150 performs transmission and reception of signals with another computer using a communication apparatus, for example, and receives measurement data from a blood pressure measurement apparatus. The communication apparatus often uses a communication scheme based on which data can be mutually exchanged at a short distance, and for example, uses a near-field wireless communication scheme, specific examples of which include communication schemes such as Bluetooth (registered trademark), TransferJet (registered trademark), ZigBee (registered trademark), and IrDA (registered trademark).

Also, a program for executing the operations performed by the pattern classification unit 903, the summary generation unit 904, and the data visualization unit 906 may also be stored in the above-described ROM 1402 or the auxiliary storage apparatus 1404, and the program may be executed by the CPU 1401. Alternatively, the program may also be stored in a server or the like separate from the information processing system 100, and may also be executed by the CPU of the server or the like. In this case, the degree of reliability can be obtained by transmitting the time-series data of the pressure pulse wave (or the time-series data of the blood pressure values) measured by the blood pressure measurement apparatus 101 to the server and performing processing in the server. In this case, there is a possibility that the processing speed will increase since the processing is performed in the server. Furthermore, the apparatus portions of the pattern classification unit 903, the summary generation unit 904, and the data visualization unit 906 are removed from the information processing system 100, and therefore the size and mass of the information processing system 100 are smaller, and the sensors can be easily arranged at positions at which measurement can be performed accurately. As a result, the burden on the user can be reduced, and accurate measurement of biological information can be easily performed.

The apparatus of the present invention can be realized also by a computer or a program, and the program can be recorded in a recording medium and can be provided via a network.

Also, the above-described apparatuses and the apparatus portions thereof can be implemented by any hardware configuration or combination configuration of hardware resources and software. A program for causing a computer to perform functions of the apparatuses by being installed in a computer in advance from a network or a computer-readable recording medium and being executed by a processor of the computer is used as the software of the combination configuration.

Note that the present invention is not limited to the above-described embodiment as-is, and can be realized with modifications to the constituent elements without departing from the gist in the implementation stage. Also, various aspects of the invention can be formed through suitable combinations of the multiple constituent elements disclosed in the above-described embodiment. For example, several constituent elements may also be removed from all of the constituent elements shown in the embodiment. Furthermore, the constituent elements of different embodiments may also be combined as appropriate.

Also, a portion or all of the above-described embodiment can be described as in the following supplementary notes, but there is no limitation to the following description.

Supplementary Note 1

An information processing apparatus comprising: a hardware processor; and a memory that is coupled to the hardware processor,
wherein the hardware processor is configured to:
classify a blood pressure surge determined with reference to time-series data of blood pressure values that change in conjunction with heartbeats, into one or more patterns based on a feature point and a feature amount that characterize the blood pressure surge; and
display, upon one of the classified patterns being selected, a waveform that corresponds to the selected pattern, or a period in the time-series data to which the waveform corresponds.

Supplementary Note 2

An information processing method comprising the steps of:
classifying, using at least one hardware processor, a blood pressure surge determined with reference to time-series data of blood pressure values that change in conjunction with heartbeats, into one or more patterns based on a feature point and a feature amount that characterize the blood pressure surge; and
displaying, using at least one hardware processor, upon one of the classified patterns being selected, a waveform that corresponds to the selected pattern, or a period in the time-series data to which the waveform corresponds.

The invention claimed is:

1. An information processing apparatus comprising:
a blood pressure measurement apparatus configured to take a blood pressure continuously;
a memory that stores a plurality of patterns each representing a blood pressure surge pattern among a plurality of blood pressure surge patterns, and the measured blood pressure as time-series data for a predetermined length of time;
a display; and
a processor configured to process the time-series data of the measured blood pressure and configured to:
generate an envelope curve connecting systolic blood pressure values in the time-series data of the measured blood pressure;
identify, within the envelope curve, a peak point, an elevation time from a first predetermined low level point, which is a start point, before the peak point to the peak point, and a lowering time from the peak point to a second predetermined low level point, which is an end point, after the peak point;
detect one blood pressure surge pattern along the envelope curve based on an analysis of the peak point, the elevation time, and the lowering time, the one blood pressure surge pattern extending from the first predetermined low level point to the second predetermined low level point; and
select a blood pressure surge pattern among the plurality of blood pressure surge patterns that matches with the one blood pressure surge pattern, and control the display to display the time-series data of the measured blood pressure and a period in the time-series data in which the one blood pressure surge pattern appeared, together with the selected pattern.

2. The information processing apparatus according to claim 1, wherein the processor is further programed to display the time-series data of the measured blood pressure in a graph.

3. The information processing apparatus according to claim 1,
wherein the processor is further configured to detect the one blood pressure surge pattern when the envelope curve includes:
a time period corresponding to the elevation time that is greater than a first threshold;
a pressure difference between a blood pressure value at the start point and a blood pressure value at the peak point that is greater than a second threshold; and
a time period corresponding to the lowering time that is greater than a third threshold.

4. The information processing apparatus according to claim 3, wherein
the first threshold includes a first predetermined plural number of heartbeats; and
the third threshold includes a second predetermined plural number of heartbeats.

5. An information processing method comprising the steps of:
measuring blood pressure with a blood pressure measurement apparatus continuously;
storing, in a memory, a plurality of patterns each representing a blood pressure surge pattern among a plurality of blood pressure surge patterns, and the measured blood pressure as time-series data for a predetermined length of time;
with a processor:
generating an envelope curve connecting systolic blood pressure values in the time-series data of the measured blood pressure;
identifying, within the envelope curve, a peak point, an elevation time from a first predetermined low level point, which is a start point, before the peak point to the peak point, and a lowering time from the peak point to a second predetermined low level point, which is an end point, after the peak point;
detecting one blood pressure surge pattern along the envelope curve based on an analysis of the peak point, the elevation time, and the lowering time, the one blood pressure surge pattern extending from the first predetermined low level point to the second predetermined low level point; and
selecting blood pressure surge pattern among the plurality of blood pressure surge patterns that matches with the one blood pressure surge pattern; and
displaying, on a display, the time-series data of the measured blood pressure and a period in the time-series data in which the one blood pressure surge pattern appeared, together with the selected pattern.

6. The method according to claim 5, further comprising detecting, with the processor, the one blood pressure surge pattern given that the envelope curve includes:
a time period corresponding to the elevation time that is greater than a first threshold;
a pressure difference between a blood pressure value at the start point and a blood pressure value at the peak point that is greater than a second threshold; and
a time period corresponding to the lowering time that that is greater than a third threshold.

7. The method according to claim 6, wherein
the first threshold includes a first predetermined plural number of heartbeats; and
the third threshold includes a second predetermined plural number of heartbeats.

* * * * *